United States Patent [19]
Witt et al.

[11] Patent Number: 5,893,835
[45] Date of Patent: Apr. 13, 1999

[54] ULTRASONIC CLAMP COAGULATOR APPARATUS HAVING DUAL ROTATIONAL POSITIONING

[75] Inventors: David Alan Witt, Loveland; Gregory D. Bishop, West Chester, both of Ohio

[73] Assignee: Ethicon Endo-Surgery, Inc., Cincinnati, Ohio

[21] Appl. No.: 08/948,911

[22] Filed: Oct. 10, 1997

[51] Int. Cl.[6] .................................................. A61B 17/32
[52] U.S. Cl. ................................. 601/2; 606/1; 606/205
[58] Field of Search ........................... 606/1, 205–208; 604/22; 601/2

[56] References Cited

U.S. PATENT DOCUMENTS

| | | |
|---|---|---|
| 4,522,206 | 6/1985 | Whipple et al. . |
| 4,979,939 | 12/1990 | Shiber .................................. 606/159 |
| 5,322,055 | 6/1994 | Davison et al. . |
| 5,330,502 | 7/1994 | Hassler et al. ......................... 606/250 |
| 5,403,342 | 4/1995 | Tovey et al. ........................... 606/205 |
| 5,468,250 | 11/1995 | Paraschac et al. ..................... 606/205 |
| 5,653,721 | 8/1997 | Knodel et al. . |

FOREIGN PATENT DOCUMENTS

| | | |
|---|---|---|
| 8-275948 | 10/1996 | Japan . |
| 8-275949 | 10/1996 | Japan . |
| 8-275951 | 10/1996 | Japan . |
| 9-98980 | 4/1997 | Japan . |

OTHER PUBLICATIONS

UltraCision Incorporated, Harmonic Scalpel Operating Manual, Ref. N Mar. 1995, 53 pages.
UltraCision Incorporated, Harmonic Scalpel Price List, Jul. 1995, 7 pages.
UltraCision Incorporated, The Harmonic Scalpel for Gynecological Surgery, 1993, 4 pages.
UltraCision CS/LS Layout, Jul. 24, 1995, 2 pages.
Snowden–Spencer, Inc., Endoscopic Plastic Surgery, 1993, 10 pages.

*Primary Examiner*—Francis J. Jaworski

[57] ABSTRACT

An ultrasonic surgical clamp coagulator apparatus is configured to effect cutting, coagulation, and clamping of tissue by cooperation of a clamping mechanism of the apparatus with an associated ultrasonic end-effector. Rotational positioning of an elongated portion and end-effector is achieved by the provision of a clutch mechanism incorporated into a housing apparatus. The arrangement permits the elongated portion to be rotatably positioned with respect to the apparatus housing and permits rotation of a the end-effector relative to the elongated portion.

26 Claims, 8 Drawing Sheets

ULTRASONIC CLAMP COAGULATOR APPARATUS HAVING DUAL ROTATIONAL POSITIONING

FIELD OF THE INVENTION

The present invention relates generally to ultrasonic surgical devices, and more particularly to an ultrasonic surgical clamp coagulator apparatus for coagulating and/or cutting tissue, including a clutch mechanism to permit rotational positioning of an ultrasonic end-effector with respect to an associated clamp arm, with end-effector, clamp arm, and associated ultrasonic drive unit thereafter being selectively rotatably positionable in an indexed manner with respect to a housing of the apparatus.

BACKGROUND OF THE INVENTION

Ultrasonic surgical instruments are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and hemostasis by coagulation, desirably minimizing patient trauma. The cutting action is typically effected by an end-effector at the distal end of the instrument, with the end-effector transmitting ultrasonic energy to tissue brought into contact therewith. Ultrasonic instruments of this nature can be configured for open surgical use, or laparoscopic or endoscopic surgical procedures.

Ultrasonic surgical instruments have been developed that include a clamp mechanism to press tissue against the end-effector of the instrument in order to couple ultrasonic energy to the tissue of a patient. Such an arrangement (sometimes referred to as an ultrasonic transector) is disclosed in U.S. Pat. No. 5,322,055, hereby incorporated by reference. However, typical constructions have included a clamp mechanism mounted in a fixed orientation relative to the handle or hand piece of the instrument. As such, a surgeon has typically been required to physically rotate the entire instrument in order to change the rotational orientation of the clamping mechanism. This can detract from convenient use of the instrument. In addition, conventional ultrasonic devices usually only use a single blade surface to cut or coagulate tissue. Therefore, a surgeon may have to change instruments for different cutting and coagulation applications.

SUMMARY OF THE INVENTION

In view of the above, an ultrasonic surgical clamp coagulator apparatus is provided to permit selective cutting, coagulation, and clamping of tissue during surgical procedures. In order to promote convenient and efficient use of the apparatus, a clamping mechanism can be selectively rotationally positioned with respect to the housing of the clamp coagulator apparatus thus permitting a surgeon to selectively position the clamping mechanism as may be required without effecting rotational manipulation of the housing. The clamp mechanism and an end-effector can be rotated together to maintain a particular end-effector configuration in alignment with the clamp mechanism.

The surgical clamp coagulator apparatus includes a clutch mechanism that permits the end-effector to be rotationally positioned with respect to the clamp mechanism to allow different end effector configurations to be aligned with the clamp mechanism for desired cutting and coagulation of tissue. The end-effector, clamp mechanism, and associated ultrasonic drive unit can thereafter be rotated as a unit, with efficient and convenient use of the clamp coagulator apparatus promoted by the provision of a detent mechanism which functions to provide indexed rotational positioning of the clamping mechanism and end-effector with respect to the housing.

In accordance with the illustrated embodiment, the present ultrasonic surgical clamp coagulation apparatus includes a housing which preferably includes a handgrip portion. The apparatus further includes an elongated portion (which may be configured for endoscopic use), including an outer tubular sheath having a proximal end rotatably joined to the housing, and a distal end positionable at the region at which tissue cutting, coagulation, and/or clamping is to be effected. In the preferred embodiment, a rotation knob is mounted on the outer tubular sheath for effecting indexed rotation of the outer sheath with respect to the apparatus housing.

An actuating member is reciprocably positioned within the outer tubular sheath, and is operatively connected with the outer sheath for rotation therewith with respect to the housing. Reciprocation of the actuating member effects the desired operation of a clamping mechanism of the clamp coagulator apparatus provided at the distal end of the outer sheath.

An ultrasonic waveguide is positioned within and extends the length of the outer tubular sheath. The ultrasonic waveguide includes an end-effector at the distal end thereof, with the end-effector extending distally of the distal end of the outer tubular sheath. The end-effector, sometimes referred to as a "blade", is ultrasonically driven by a transducer of an associated ultrasonic drive unit so that longitudinal ultrasonic vibration of the end-effector effects the desired tissue cutting and coagulation. The waveguide can be joined for rotation together with the outer sheath, with the drive unit also coupled for rotation therewith. The waveguide as well as the drive unit can also be rotated with respect to the outer tubular sheath and the clamping mechanism.

The clamping mechanism of the clamp coagulator apparatus includes a clamp arm pivotally mounted on the distal end of the outer tubular sheath for pivotal movement with respect to the end-effector. Tissue is clamped between the clamp arm and the end-effector, thereby ultrasonically coupling the tissue with the end-effector (when energized) or permitting grasping and clamping of tissue when ultrasonic energy is not being transmitted through the waveguide to the end-effector. The clamp arm is operatively connected to the reciprocable actuating member of the clamp coagulator apparatus so that reciprocable movement of the actuating member pivotally moves the clamp arm with respect to the end-effector.

Selective operation of the clamping mechanism is provided by an operating lever pivotally connected to the apparatus housing. In the preferred embodiment, the operating lever, and associated handgrip portion of the housing are provided with a scissors-like configuration, thus permitting convenient movement of the operating lever by a user's thumb. The operating lever is interconnected with the reciprocable actuating member by an actuator collar so that pivotal movement of the operating lever reciprocally moves the actuating member for pivotally moving the clamp arm of the clamp coagulator apparatus.

The clamp coagulator apparatus also includes a detent mechanism that permits indexed rotational movement of the outer sheath (and preferably the waveguide and associated drive unit) relative to the housing. Notably, a clutch mechanism is provided that allows selective rotational movement of the waveguide with respect to the housing and outer sheath when the clutch mechanism is disengaged from the rotational knob. The clutch mechanism cooperatively engages with the rotational knob so that a selected end effector configuration is maintained in alignment with the clamping member. The waveguide and end-effector, and the associated ultrasonic drive unit, can then be rotated as a unit with the clamping mechanism relative to the housing of the apparatus.

In order to provide the desired indexed rotational movement of the clamping mechanism, the detent mechanism includes at least one spring-biased detent in the apparatus housing, with the rotation knob defining a detent-receiving surface engaged by the detent and cooperating therewith to provide indexed rotation of the clamping member, and accordingly, indexed rotation of the outer sheath with respect to the apparatus housing. The detent-receiving surface of the rotational knob preferably defines a plurality of circumferentially spaced radial depressions therebetween for receiving the spring-biased detent on the housing.

Further features and advantages of the present invention will become readily apparent from the following detailed description, the accompanying drawings, and the appended claims.

DETAILED DESCRIPTION

While the present invention is susceptible of embodiments in various forms, there is shown in the drawings and will hereinafter be described presently preferred embodiments, with the understanding that the present disclosure is to be considered as an exemplification of the invention, and is not intended to limit the invention to the specific embodiments illustrated.

The present invention is particularly directed to an improved ultrasonic surgical clamp coagulator apparatus which is configured for effecting tissue cutting, coagulation, and/or clamping during surgical procedures. The present apparatus can readily be configured for use in both open surgical procedures, as well as laparoscopic or endoscopic procedures. As will become apparent from the following description, the present clamp coagulator apparatus is particularly configured for disposable use by virtue of its simple construction. As such, it is contemplated that the apparatus be used in association with an ultrasonic drive unit of a surgical system, whereby ultrasonic energy from the drive unit provides the desired ultrasonic actuation of the clamp coagulator apparatus. It will be appreciated that a clamp coagulator apparatus can be configured for non-disposable use, and non-detachably integrated with an associated ultrasonic drive unit. However, detachable connection of the present clamp coagulator apparatus with an associated ultrasonic drive unit is presently preferred for single-patient use of the apparatus.

Figures 1, 2:
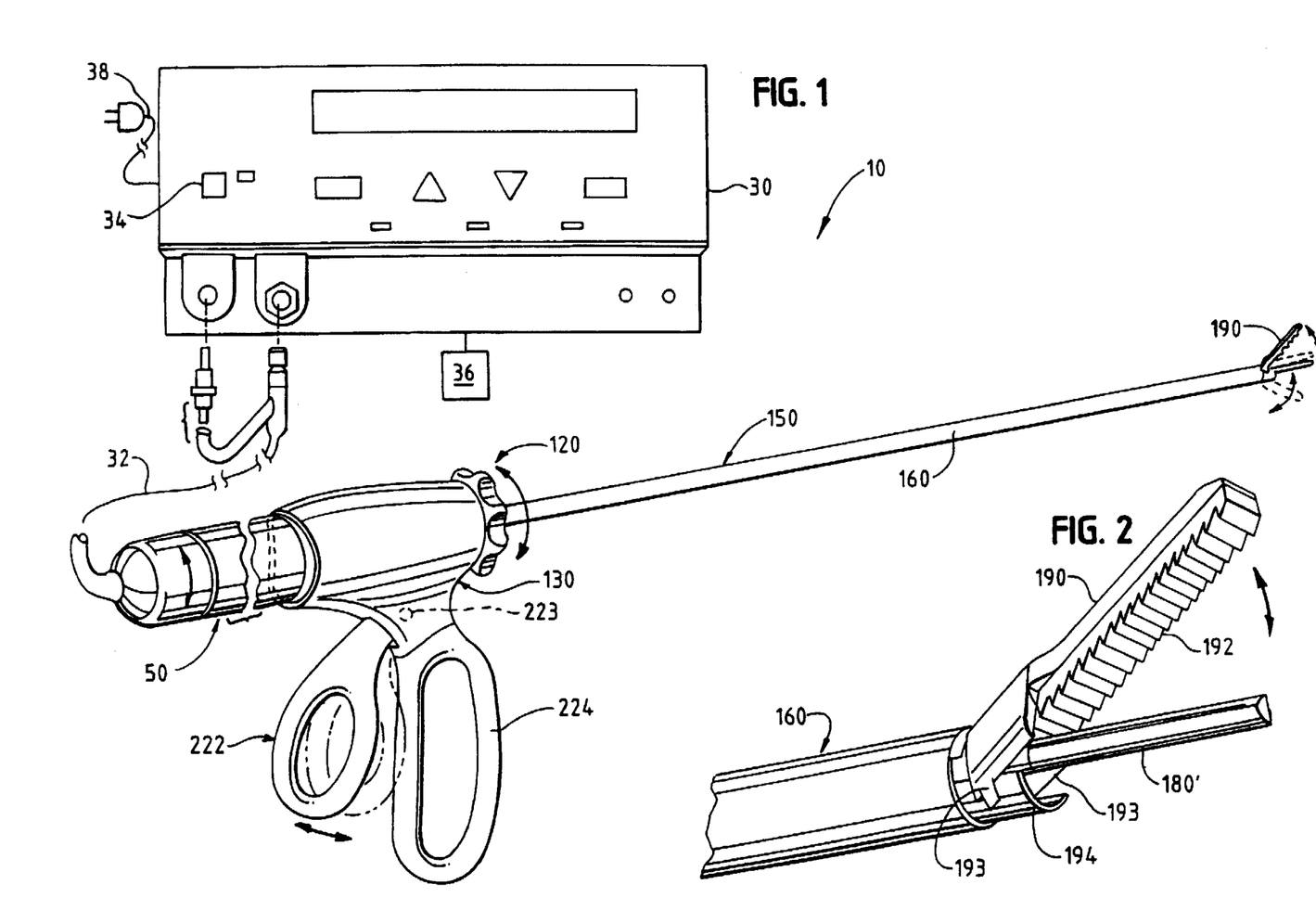
FIG. 1 is a perspective view of an ultrasonic surgical system including an ultrasonic clamp coagulator apparatus in accordance with the present invention.
FIG. 2 is an enlarged, fragmentary perspective view of a clamp mechanism of the clamp coagulator apparatus illustrated in FIG. 1.
Figure 3:
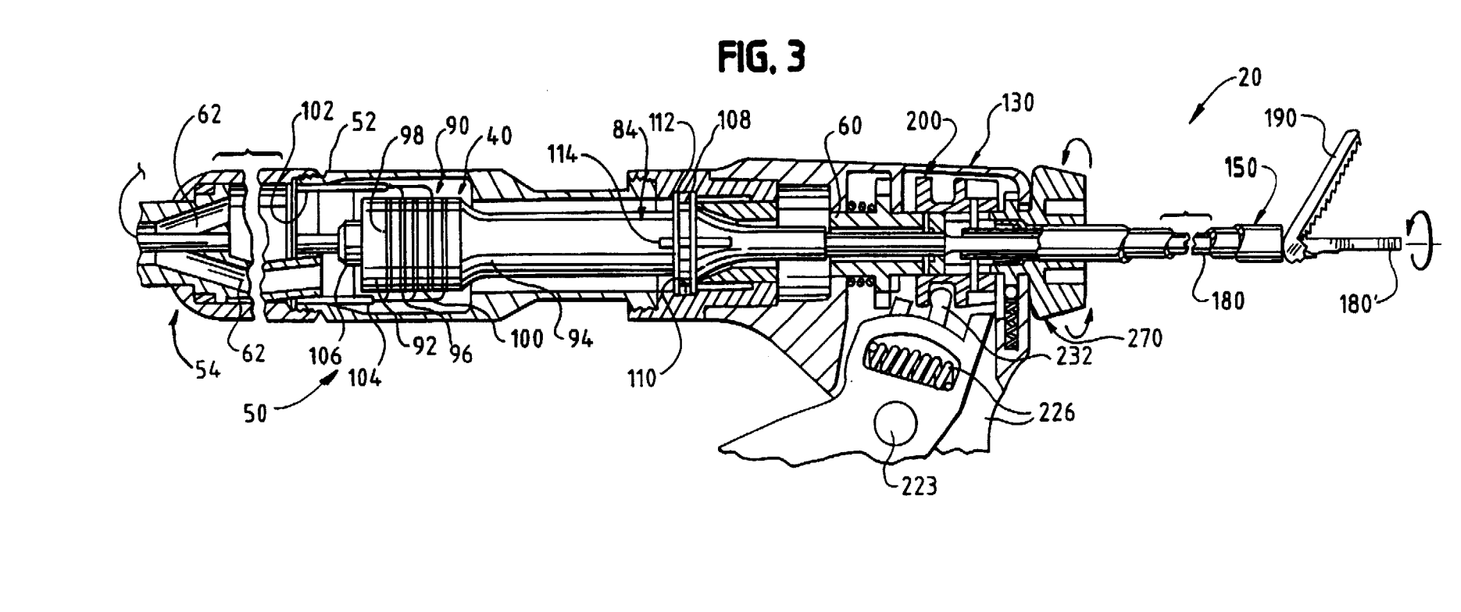
FIG. 3 is a side elevational view, partially in cross-section, of the clamp coagulator apparatus in accordance with the present invention, shown in operative association with an ultrasonic drive unit of the surgical system shown in FIG. 1.

With reference to FIGS. 1 and 3, therein is illustrated a presently preferred embodiment of a surgical system, generally designated 10, which includes an ultrasonic clamp coagulator apparatus embodying the principles of the present invention. Preferred details of the ultrasonic generator and associated ultrasonic drive unit of the surgical system 10 will first be described, with subsequent detailed description of the ultrasonic surgical clamp coagulator apparatus, including a clamp mechanism configured for indexed rotation, and an end-effector configured for rotational movement with respect to the clamp mechanism.

The surgical system 10 includes an ultrasonic generator 30 and an associated ultrasonic surgical instrument. The surgical instrument includes an ultrasonic drive unit, designated 50, and an ultrasonic clamp coagulator apparatus 120 embodying the principles of the present invention. As will be further described, an ultrasonic transducer and mounting device of the drive unit 50, and an ultrasonic waveguide of the clamp coagulator apparatus 120, provide an acoustic assembly of the present surgical system, with the acoustic assembly providing ultrasonic energy for surgical procedures when powered by the generator 30. It will be noted that in some applications, the ultrasonic drive unit 50 is referred to as a "hand piece assembly" because the surgical instrument of the surgical system 10 is configured such that a surgeon grasps and manipulates the ultrasonic drive unit 50 during various procedures and operations. As shown in FIG. 1, the clamp coagulator apparatus 120 of the surgical system preferably includes a scissors-like grip arrangement which facilitates positioning and manipulation of the instrument apart from manipulation of the ultrasonic drive unit 50.

The generator 30 of the surgical system sends an electrical signal through a cable 32 at a selected excursion, frequency, and phase determined by a control system of the generator 30. As will be further described, the signal causes one or more piezoelectric elements of the acoustic assembly of the surgical instrument to expand and contract, thereby converting the electrical energy into mechanical motion. The mechanical motion results in longitudinal waves of ultrasonic energy that propagate through the acoustic assembly in an acoustic standing wave to vibrate the acoustic assembly at a selected frequency and excursion. An end-effector at the distal end of the waveguide of the acoustic assembly is placed in contact with tissue of the patient to transfer the ultrasonic energy to the tissue. As further described below, a surgical tool, such as, a jaw or clamping mechanism, is preferably utilized to press the tissue against the end-effector.

As the end-effector couples with the tissue, thermal energy or heat is generated as a result of friction, acoustic absorption and viscous losses within the tissue. The heat is sufficient to break protein hydrogen bonds, causing the highly structured protein (i.e., collagen and muscle protein) to denature (i.e., become less organized). As the proteins are denatured, a sticky coagulum forms to seal or coagulate small blood vessels. Deep coagulation of larger blood vessels results when the effect is prolonged.

The transfer of the ultrasonic energy to the tissue causes other effects including mechanical tearing, cutting, cavitation, cell disruption, and emulsification. The amount of cutting as well as the degree of coagulation obtained varies with the excursion of the end-effector, the frequency of vibration, the amount of pressure applied by the user, the sharpness of the end-effector, and the coupling between the end-effector and the tissue.

As illustrated in FIG. 1, the generator 30 includes a control system integral with the generator 30, a power switch 34, triggering mechanism 36. The power switch 34 controls the electrical power to the generator 30, and when activated by the triggering mechanism 36, the generator 30 provides energy to drive the acoustic assembly of the surgical system 10 at a predetermined frequency and to drive the end-effector at a predetermined excursion level. The generator 30 can drive or excite the acoustic assembly at any suitable resonant frequency of the acoustic assembly.

When the generator 30 is activated via the triggering mechanism 36, electrical energy is continuously applied by the generator 30 to a transducer stack or assembly 40 of the acoustic assembly as shown in FIG. 3. A phase-locked loop in the control system of the generator 30 monitors feedback from the acoustic assembly. The phase lock loop adjusts the frequency of the electrical energy sent by the generator 30 to match the resonant frequency of the selected longitudinal mode of vibration of the acoustic assembly including the tissue load. In addition, a second feedback loop in the control system maintains the electrical current supplied to the acoustic assembly at a preselected constant level in order to achieve substantially constant excursion at the end-effector of the acoustic assembly.

The electrical signal supplied to the acoustic assembly will cause the distal end of the end-effector to vibrate longitudinally in the range of, for example, approximately 20 kHz to 250 kHz, and preferably in the range of about 54 kHz to 56 kHz, and most preferably at about 55.5 kHz. The excursion of the vibrations at the end-effector can be controlled by, for example, controlling the amplitude of the electrical signal applied to the transducer assembly 40 of the acoustic assembly by the generator 30.

As noted above, the triggering mechanism 36 of the generator 30 allows a user to activate the generator 30 so that electrical energy may be continuously supplied to the acoustic assembly. The triggering mechanism 36 preferably comprises a foot activating switch that is detachably coupled or attached to the generator 30 by a cable or cord. Alternatively, the triggering mechanism can be configured as a hand switch incorporated in the ultrasonic drive unit 50 to allow the generator 30 to be activated by a user.

The generator 30 also has a power line 38 for insertion in an electro-surgical unit or conventional electrical outlet. It is contemplated that the generator 30 can also be powered by a direct current (DC) source, such as a battery. The generator 30 can comprise any suitable generator, such as Model No. GEN01, available from Ethicon Endo-Surgery, Inc.

Referring to FIGS. 1 and 3, the ultrasonic drive unit 50 of the surgical instrument includes a multi-piece housing 52 adapted to isolate the operator from the vibrations of the acoustic assembly. The drive unit housing 52 can be shaped to be held by a user in a conventional manner, but it is contemplated that the present clamp coagulator apparatus 120 principally be grasped and manipulated by a scissors-like arrangement provided by a housing of the clamp coagulator apparatus, as will be described below. While the multi-piece housing 52 is illustrated, the housing 52 may comprise a single or unitary component.

The housing 52 of the ultrasonic drive unit 50 generally includes a proximal end, a distal end, and a cavity extending longitudinally therein. The distal end of the housing 52 includes an opening 60 configured to allow the acoustic assembly of the surgical system 10 to extend therethrough, and the proximal end of the housing 52 is coupled to the generator 30 by a cable 32. The cable 32 preferably includes ducts or vents 62 to allow air to be introduced into the housing 52 of the ultrasonic drive unit 50 to cool the transducer assembly 40 of the acoustic assembly.

The housing 52 of the ultrasonic drive unit 50 is preferably constructed from a durable plastic, such as Ultem®. It is also contemplated that the housing 52 may alternatively be made from a variety of materials including other plastics (i.e. liquid crystal polymer (LCP), nylon, or polycarbonate). A suitable ultrasonic drive unit 50 is Model No. HP050, available from Ethicon Endo-Surgery, Inc.

As shown in FIG. 3, the acoustic assembly includes a transducer stack or assembly 40 and a mounting device 84 which are preferably carried by the ultrasonic drive unit 50, and a transmission component or working member, referred to herein as the waveguide having an end-effector, which are carried by the ultrasonic clamp coagulator apparatus. The components of the acoustic assembly are preferably acoustically tuned such that the length of each component is an integral number of one-half wavelengths ($n\lambda/2$), where the wavelength $\lambda$ is the wavelength of a preselected or operating longitudinal vibration frequency $f_0$ of the acoustic assembly, and n is any non-negative integer. It is also contemplated that the acoustic assembly may incorporate any suitable arrangement of acoustic elements.

The transducer assembly 40 of the acoustic assembly converts the electrical signal from the generator 30 into mechanical energy that results in longitudinal vibratory motion of the end-effector at ultrasonic frequencies. When the acoustic assembly is energized, a vibratory motion standing wave is generated through the acoustic assembly. The excursion of the vibratory motion at any point along the acoustic assembly depends on the location along the acoustic assembly at which the vibratory motion is measured. A minimum or zero crossing in the vibratory motion standing wave is generally referred to as a node (i.e., where motion is usually minimal), and an absolute value maximum or peak in the standing wave is generally referred to as an anti-node. The distance between an anti-node and its nearest node is one-quarter wavelength ($\lambda/4$).

As shown in FIG. 3, the transducer assembly 40 of the acoustic assembly, which is also known as a "Langevin stack", generally includes a transduction portion 90, a first resonator 92, and a second resonator 94. The transducer assembly is preferably an integral number of one-half system wavelengths (nλ/2) in length. It is to be understood that the present invention may be alternatively configured to include a transducer assembly comprising a magnetostrictive, electromagnetic or electrostatic transducer.

The distal end of the first resonator 92 is connected to the proximal end of transduction section 90, and the proximal end of the second resonator 94 is connected to the distal end of transduction portion 90. The first and second resonators 92 and 94 are preferably fabricated from titanium, aluminum, steel, or any other suitable material, and most preferably, the first resonator 92 is fabricated from 303 stainless steel and the second resonator 94 is fabricated from 7075-T651 Aluminum. The first and second resonators 92 and 94 have a length determined by a number of variables, including the length of the transduction section 90, the speed of sound of the material used in the resonators 92 and 94, and the desired fundamental frequency $f_o$ of the transducer assembly 40. The second resonator 94 can be tapered inwardly from its proximal end to its distal end to function as a velocity transformer and amplify the ultrasonic vibration excursion.

The transduction portion 90 of the transducer assembly 40 preferably comprises a piezoelectric section of alternating positive electrodes 96 and negative electrodes 98, with piezoelectric elements 100 alternating between the electrodes 96 and 98. The piezoelectric elements 100 can be fabricated from any suitable material, such as, for example, lead zirconate-titanate, lead meta-niobate, lead titanate, or other piezoelectric material. Each of the positive electrodes 96, negative electrodes 98, and piezoelectric elements 100 have a bore extending through the center. The positive and negative electrodes 96 and 98 are electrically coupled to wires 102 and 104, respectfully. The wires 102 and 104 transmit the electrical signal from the generator 30 to electrodes 96 and 98.

As illustrated in FIG. 3, the piezoelectric elements 100 are held in compression between the first and second resonators 92 and 94 by a bolt 106. The bolt 106 preferably has a head, a shank, and a threaded distal end. The bolt 106 is inserted from the proximal end of the first resonator 92 through the bores of the first resonator 92, the electrodes 96 and 98, and the piezoelectric elements 100. The threaded distal end of the bolt 106 is screwed into a threaded bore in the proximal end of second resonator 94. The bolt can be fabricated from steel, titanium, aluminum, or other suitable material and is preferably fabricated from Ti-6Al-4V Titanium, and most preferably from 4037 low alloy steel.

The piezoelectric elements 100 are energized in response to the electrical signal supplied from the generator 30 to produce an acoustic standing wave in the acoustic assembly. The electrical signal causes an electromagnetic field across the piezoelectric elements 100, causing the piezoelectric elements 100 to expand and contract in a continuous manner along the axis of the voltage gradient, producing high frequency longitudinal waves of ultrasonic energy. The ultrasonic energy is transmitted through the acoustic assembly to the end-effector.

The mounting device 84 of the acoustic assembly has a proximal end, a distal end, and preferably has a length substantially equal to an integral number of one-half system wavelengths. The proximal end of the mounting device 84 is preferably axially aligned and coupled to the distal end of the second resonator 94 by a threaded connection near an anti-node. (For purposes of this disclosure, the term "near" is defined as "exactly at" or "in close proximity to".) It is also contemplated that the mounting device 84 may be attached to the second resonator 94 by any suitable means, and the second resonator 94 and mounting device 84 may be formed as a single or unitary component.

The mounting device 84 is coupled to the housing 52 of the ultrasonic drive unit 50 near a node. The mounting device 84 preferably includes an integral mounting flange 108 disposed around its periphery. The mounting flange 108 is preferably disposed in an annular groove 110 formed in the housing 52 of the ultrasonic drive unit 50 to couple the mounting device 84 to the housing 52. A compliant member or material 112, such as a pair of silicone rubber O-rings attached by stand-offs, may be placed between the annular groove 110 of the housing 52 and the integral flange 108 of the mounting device 84 to reduce or prevent ultrasonic vibration from being transmitted from the mounting device 84 to the housing 52.

The mounting device 84 is preferably secured in a predetermined axial position by a plurality of pins 114, preferably four. The pins 114 are disposed in a longitudinal direction and ninety (90) degrees apart from each other around the outer periphery of the mounting device 84. The pins 114 are coupled to the housing 52 of the ultrasonic drive unit 50 and are disposed through notches in the flange 108 of the mounting device 84. The pins 114 are preferably fabricated from stainless steel.

The mounting device 84 is preferably configured to amplify the ultrasonic vibration excursion that is transmitted through the acoustic assembly to the distal end of the end-effector. In one preferred embodiment, the mounting device 84 comprises a solid, tapered horn. As ultrasonic energy is transmitted through the mounting device 84, the velocity of the acoustic wave transmitted through the mounting device 84 is amplified. It is contemplated that the mounting device 84 can be configured as any suitable shape, such as, for example, a stepped horn, a conical horn, an exponential horn, a unitary gain horn, or the like.

As shown in FIG. 3, the mounting device 84 is preferably acoustically coupled to the waveguide 180 which is carried by the ultrasonic clamp coagulator apparatus 120. The distal end of the mounting device 84 is preferably coupled to the proximal end of the waveguide 180 by a threaded connection near an anti-node, but alternative coupling arrangements can be employed.

Figure 4:
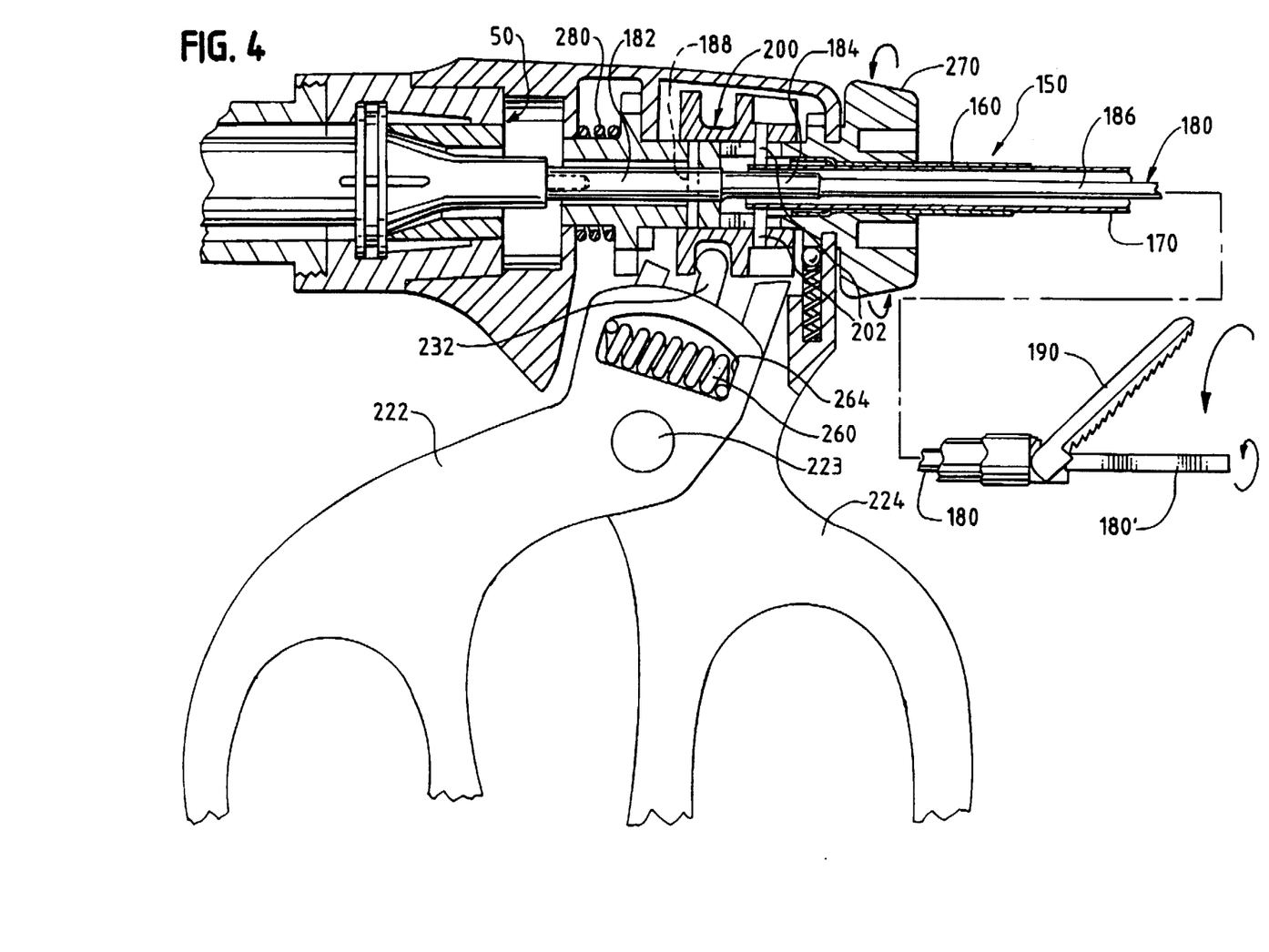
FIG. 4 is an enlarged, fragmentary view of the present clamp coagulator apparatus with the clamping mechanism in an open position.

Referring now to FIG. 4, an enlarged fragmentary view of the ultrasonic clamp coagulator apparatus 120 of the surgical system 10 with the clamp mechanism in an open position is illustrated. The proximal end of the ultrasonic clamp coagulator apparatus 120 preferably receives and is fitted to the distal end of the ultrasonic drive unit 50 by insertion of the drive unit into the housing of the clamp coagulator apparatus. The ultrasonic clamp coagulator apparatus 120 is preferably attached to and removed from the ultrasonic drive unit 50 as a unit. The ultrasonic clamp coagulator apparatus 120 can be disposed of after a single use.

The ultrasonic clamp coagulator apparatus 120 preferably includes a handle assembly or a housing 130, preferably comprising mating housing portions, and an elongated or endoscopic portion 150. The elongated portion 150 of the ultrasonic clamp coagulator apparatus 120 extends orthogonally from the housing 130. The elongated portion 150 can be selectively rotated with respect to the housing 130 as further described below. When the clamp coagulator apparatus is configured for endoscopic use, the construction can be dimensioned such that endoscopic portion 150 has an outside diameter of about 5.5 mm.

As illustrated in FIGS. 1, 3, and 4, the elongated portion 150 preferably includes an outer tubular member or sheath 160, an inner tubular actuating member 170, and the waveguide 180 having an end-effector 180'. As will be described, the outer sheath 160, the actuating member 170, and the waveguide 180 are preferably joined together for indexed rotation as a unit (together with ultrasonic drive unit 50) relative to housing 130. The waveguide 180 is also configured for rotation with respect to the outer sheath 160 and the clamp mechanism.

As illustrated in FIG. 4, the proximal end of the waveguide 180 of the acoustic assembly is preferably detachably coupled to the mounting device 84 of the ultrasonic drive unit 50 near an anti-node as described above. The waveguide 180 preferably has a length substantially equal to an integer number of one-half system wavelengths ($n\lambda/2$). The waveguide 180 is preferably fabricated from a solid core shaft constructed out of material which propagates ultrasonic energy efficiently, such as titanium alloy (i.e., Ti-6Al-4V) or an aluminum alloy. It is contemplated that the waveguide 180 can alternatively be fabricated from any other suitable material.

The waveguide is preferably substantially semi-flexible. It will be recognized that the waveguide can alternatively be substantially rigid or may comprise a flexible wire. The waveguide may be configured to amplify the mechanical vibrations transmitted through the waveguide to the end-effector as is well known in the art.

The waveguide 180 can have any suitable cross-sectional dimension. For example, the waveguide may have a substantially uniform cross-section or the waveguide may be tapered at various sections or may be tapered along its entire length. The waveguide may further have features to control the gain of the longitudinal vibration along the waveguide and features to tune the waveguide to the resonant frequency of the system.

As shown in FIG. 4, the waveguide 180 generally has a first section 182, a second section 184, and a third section 186. The first section 182 of the waveguide extends distally from the distal end of the mounting device 84, and has a substantially continuous cross-section dimension.

The first section 182 preferably includes at least one radial hole or aperture 188 extending diametrically therethrough, substantially perpendicular to the axis of the waveguide 180. The aperture 188 is preferably positioned at a node, but may be otherwise positioned. It will be recognized that the aperture 188 may have any suitable depth and may be any suitable shape. The aperture is configured to receive a connector pin member which connects or couples the waveguide 180 to a reciprocable clutch mechanism 220 as further described below.

The second section 184 of the waveguide 180 extends distally from the first section 182. The second section 184 preferably also has a substantially continuous cross-section. The diameter of the second section 184 is smaller than the diameter of the first section 182 and larger than the diameter of the third section 186. As ultrasonic energy passes from the first section 182 of the waveguide 180 into the second section 184, the narrowing of the second section 184 will result in an increased amplitude of the ultrasonic energy passing therethrough.

The third section 186 extends distally from the distal end of the second section 184. The third section 186 also has a substantially continuous cross-section. The third section 186 may also include small diameter changes along its length. As ultrasonic energy passes from the second section 184 of the waveguide 180 into the third section 186, the narrowing of the third section 186 will result in an increased amplitude of the ultrasonic energy passing therethrough.

The third section 186 may have a plurality of grooves or notches (not shown) formed in its outer circumference. The grooves may be located at nodes of the waveguide 180 to act as alignment indicators for the installation of a damping sheath (not shown) and stabilizing silicone rings or compliant supports during manufacturing. A seal is preferably provided at the distal-most node, nearest the end-effector 180', to abate passage of tissue, blood, and other material in the region between the waveguide and actuating member 170.

The end-effector 180' of the waveguide 180 is preferably integral therewith and formed as a single unit. The end-effector may alternately be connected by a threaded connection, or by a welded joint. The distal end of the end-effector is disposed near an anti-node in order to tune the acoustic assembly to a preferred resonant frequency $f_o$ when the acoustic assembly is not loaded by tissue. When the transducer assembly is energized, the distal end of the end-effector is configured to move longitudinally in the range of, for example, approximately 10–500 microns peak-to-peak, and preferably in the range of about 10 to about 100 microns at a predetermined vibrational frequency $f_o$.

With particular reference to FIG. 2, therein is illustrated the clamping mechanism of the present clamp coagulator apparatus 120, which is configured for cooperative action with the end-effector 180' of the waveguide 180. The clamping mechanism includes a pivotally movable clamp arm 190, which is pivotally connected at the distal end of outer tubular sheath 160. A clamp pad 192, preferably formed from Teflon or other suitable low-friction material, is mounted on the surface of the clamp arm for cooperation with the end-effector 180', with pivotal movement of the clamp arm positioning the clamp pad in substantially parallel relationship to, and in contact with, the end-effector 180'. By this construction, tissue to be clamped is grasped between the pad 192 and the end effector 180'.

As illustrated, the pad 192 of the clamp mechanism is preferably provided with a sawtooth-like configuration to enhance the gripping of tissue in cooperation with the end-effector 180'. It is also contemplated that the pad can have a longitudinal groove (i.e., a U-shaped or V-shaped groove) along its length and recessed among the sawtooth-like configuration. As further described below, the end-effector 180' can be rotated with respect to the clamp arm 190 to position a narrow or sharp edge 191a or a broad edge 191b of the end-effector 180' in alignment with the clamp pad 192.

Pivotal movement of the clamp arm 190 with respect to the end-effector 180' is effected by the provision of at least one, and preferably a pair of lever portions 193 of the clamp arm 190 at the proximal end thereof. The lever portions are positioned on respective opposite sides of the end-effector 180', and are in operative engagement with a drive portion 194 of the reciprocable actuating member 170. Reciprocable movement of the actuating member, relative to the outer tubular sheath 160 and the end-effector 180', thereby effects pivotal movement of the clamp arm relative to the end-effector. The lever portions 193 can be respectively positioned in a pair of openings defined by the drive portion 194, or otherwise suitably mechanically coupled therewith, whereby reciprocable movement of the actuating member 170 acts through the drive portion 194 and lever portions 193 to pivot the clamp arm.

With particular reference to FIGS. 3, 4, 5, and 8, reciprocable movement of the actuating member 170 is effected by the provision of an actuator collar 200 reciprocally and rotatably mounted in the housing 130 of the clamp coagulator apparatus 120. The actuator collar 200 is coupled to the proximal end of the actuating member 170 by a pair of connecting pins 202 (see FIG. 4) for conjoint rotation. The actuator collar 200 includes a pair of axially spaced apart circumferential flanges 204 defining a circumferential groove 206 (see FIG. 5).

The actuator collar 200 is operatively connected with the operating lever 222 of the clamp coagulator apparatus 120. The operating lever includes a drive member or trigger actuator 230 that is interconnected with the reciprocable actuating collar 200 (see FIG. 5). The operating lever 222 is pivotally connected to the housing 130 of the clamp coagulator apparatus (by a pivot mount 223) for cooperation in a scissors-like fashion with a handgrip portion 224 of the housing.

Figure 5:
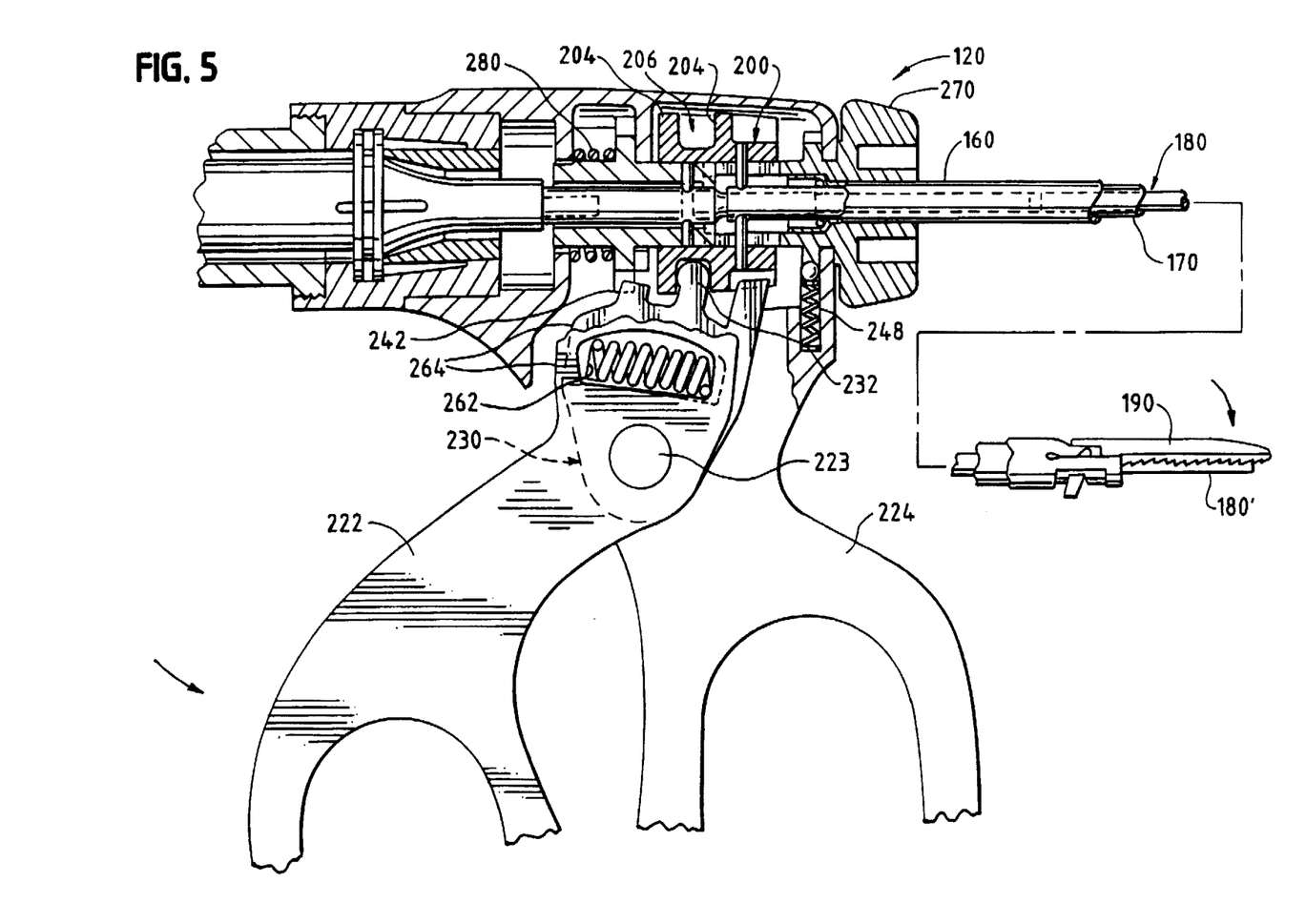
FIG. 5 is an enlarged, fragmentary view of the present clamp coagulator apparatus with the clamp mechanism in a closed position.

The drive member 230 of the operating lever 222 includes a drive lug 232 that fits in the circumferential groove 206 of the actuator collar 200 to reciprocate the actuator collar 200 when the lever 222 is moved. As shown in FIG. 5, movement of lever 222 toward handgrip portion 224 moves the drive member 230 and the actuator collar 200 to cause the connecting pins 202 to slide the actuating member 170 proximally, thereby pivoting clamp arm 190 toward end-effector 180'. When the operating lever 222 is moved away from the handgrip portion 224, drive member 230 and the actuating collar 200 move to cause the actuating member 170 to slide forwardly to open the clamp mechanism as shown in FIG. 4.

The drive member 230 of the operating lever also includes a rotational lockout member 242 to fit within notches 244 formed in a circumferential flange 246 (see FIG. 8) of the clutch mechanism 220 and a rotational lockout member 248 to fit within notches 250 formed in a circumferential flange 252 of the actuator collar 200. the lockout members 242 and 248 prevent rotation of the endoscopic portion 150 of the clamp coagulator apparatus when the clamp arm is in a closed-position as shown in FIG. 5. When the operating lever 222 is moved away from the handgrip portion to open the clamp mechanism, the lockout members 242 and 248 move out of the notches 244 and 250, respectively, to allow rotation of the end-effector with the clamp mechanism.

Operative connection of the drive member 230 with the thumb-receiving portion of the operating lever 222 is provided by a limiter spring 260, preferably comprising a compression coil spring. The spring 260 fits within a spring slot 262 defined by the drive member 230, which in turn is positioned between a pair of spring retainer flanges 264 of the operating lever 222. The drive member 230 is pivotally movable with respect to the spring flanges 264 (about pivot mount 223 of housing 130) in opposition to the compression coil spring, which bears against the surfaces of spring slots defined by each of the spring flanges 264. In this manner, the force which can be applied to the actuating member 170, by pivotal movement of operating lever 222 acting through drive member 230 and the actuator collar 200, is limited by the force with which spring 260 bears against the spring flanges 264. Application of excessive force results in pivotal displacement of drive member 230 relative to the spring flanges 264 of the operating lever 222 in opposition to the spring 260. In a presently preferred embodiment, the spring 260 is selected to limit clamping force at clamp arm 190 to approximately 2 pounds. Stop portions of housing 130 limit the travel of operating lever 222 to prevent excessive compression of spring 260.

Figures 6, 7:
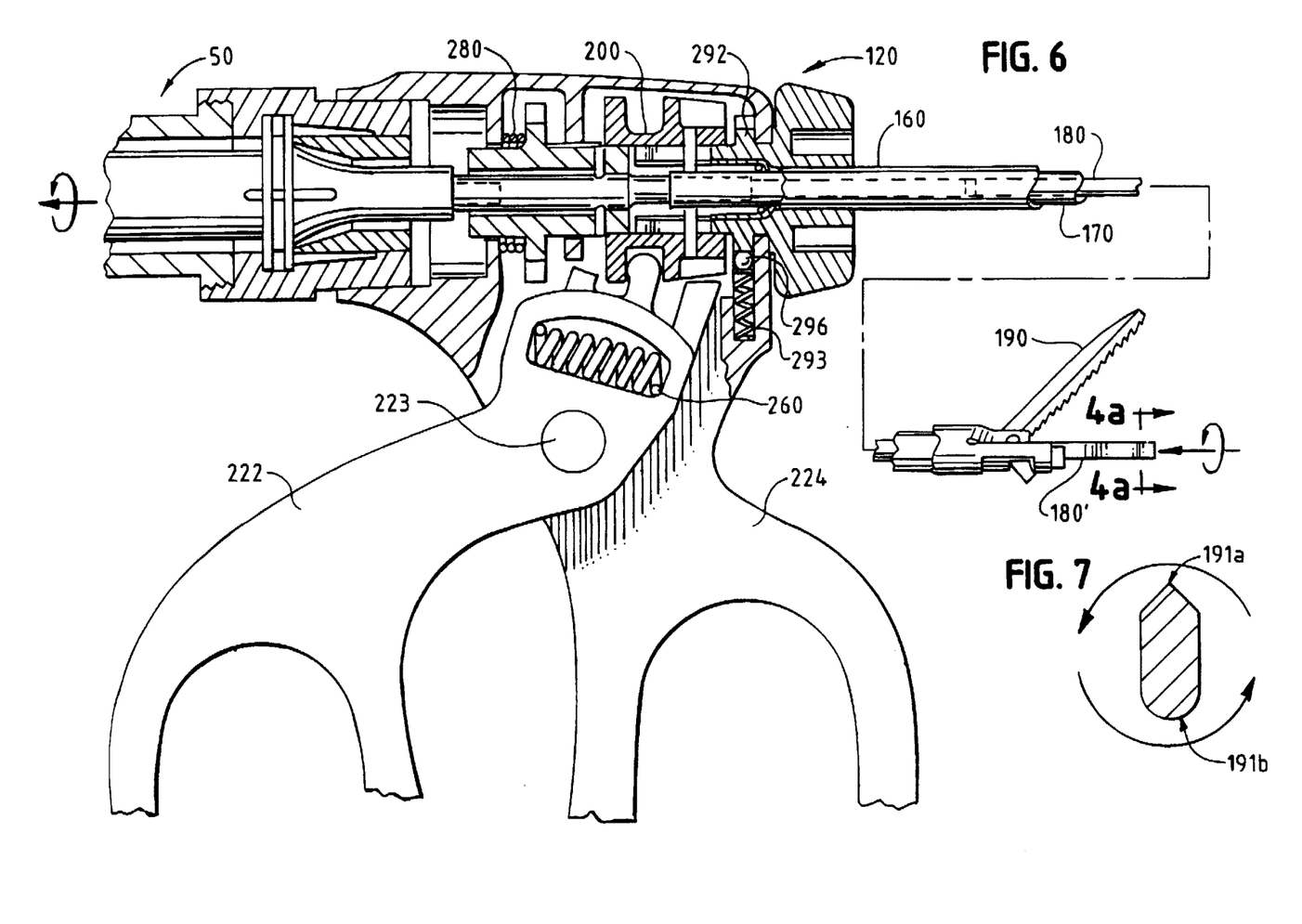
FIG. 6 is an enlarged, fragmentary view of the present clamp coagulator apparatus illustrating the rotational movement of the end-effector relative to the clamp mechanism.
FIG. 7 is a cross-section view of the end-effector taken about line 4A of FIG. 6 further illustrating the movement of the end-effector.
Figure 8:
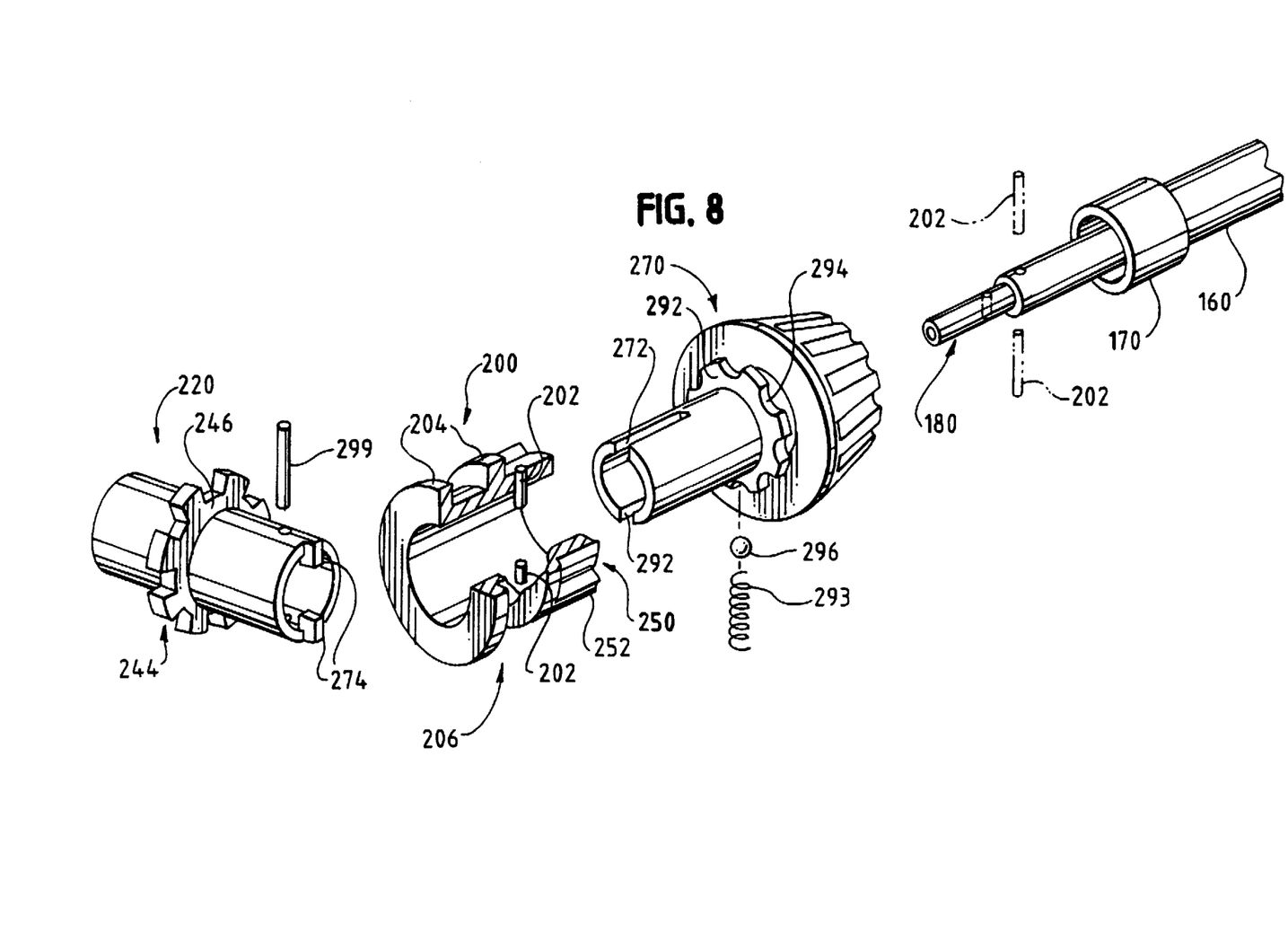
FIG. 8 is an enlarged, diagrammatic view illustrating an actuator collar, a rotational knob, and the clutch mechanism of the present clamp coagulator apparatus.

A rotation knob 270 is preferably mounted on the outer tubular sheath 170 to facilitate rotational positioning of the elongated portion 150 with respect to the housing 130 of the clamp coagulator apparatus. As shown in FIG. 8, the proximal end of the rotation knob 270 preferably includes a pair of elongated opposing openings or slots 272 to cooperatively engage with suitable locking dogs 274 at the distal end of the clutch mechanism 220. The clutch mechanism 220 is normally biased by a spring member 280 to cause the locking dogs 274 to drivingly interconnect with the opposing slots 272 of the rotational knob 270 as shown in FIGS. 4 and 7. The spring member 280 is disposed between the circumferential flange 246 of the clutch mechanism 220 and a wall of the housing 130. Preferably, the spring member 280 comprises a compression coil spring. The clutch mechanism is that configured to include a drive surface (provided by dogs 274) which is driven by the associated slots 272 of knob 270.

The elongated slots 272 of the rotational knob 270 permit the connector pins 202 to extend therethrough and to accommodate reciprocable movement of the connector pins when the actuating collar 200 is axially moved relative to the waveguide 180. When the elongated slots 272 of the knob 270 are interconnected with the locking dogs 274 of the clutch mechanism 220, rotation of the rotation knob 270 enables the elongated portion 150 including the clamp mechanism and the end-effector 180', and the associated ultrasonic drive to be turned as a unit to a selected or desired angular position.

The elongated portion 150 of the clamp coagulator apparatus 120 can be rotatably indexed by the provision of a detent mechanism incorporated in the clamp coagulator apparatus. The rotational knob 270 includes an axial flange 292 defining a detent-receiving surface. The detent-receiving surface defines a plurality of circumferentially spaced detent-receiving depression or recesses 294 generally about the periphery of the flange 292 of the rotational knob 270. In the illustrated embodiment, eight (8) recesses 294 are shown. However, it is contemplated that twelve (12) of the depressions 294 can be provided, thereby providing indexed positioning of the elongated portion 150 of the apparatus at 30° intervals relative to the housing 130 of the clamp coagulator apparatus.

Indexed rotational movement is further achieved by the provision of at least one detent 296 in the housing of the clamp coagulator apparatus. The detent 296 preferably comprises a ball that is biased into engagement with the flange 292 of the rotational knob 270 by a spring member 293 (i.e., a coil spring) for engagement with the depressions thereof. The ball cooperates with the radial depressions defined by the rotational knob 270 to resist relative rotational torque less than about 5–20 inch-ounces. As such, the elongated portion 150 of the clamp coagulator apparatus is maintained in any of its selected indexed rotational positions, relative to housing 130, unless a torque is applied (such as by rotation knob) exceeding this predetermined torque level.

When the proximal end of the rotational knob 270 is engaged with the distal end of the clutch mechanism 220 and the rotation knob 270 is turned, the end-effector 180' and clamp arm 190 are rotated simultaneously. When the drive unit 50 is pulled proximally to compress the spring 280 and to disengage the dogs 274 of the clutch mechanism 220 from the elongated slots 272 of rotation knob 270 as shown in FIG. 6, the drive unit 50 can be turned to rotate the end-effector 180' to selectively orient an edge of the end-effector 180' with respect to the clamp arm 190 of the clamp mechanism. A connector pin 299 preferably joins the clutch mechanism 220 to the waveguide 180 for rotation together relative to housing 130.

When the drive unit 50 is rotated approximately one-hundred eighty (180) degrees, the dogs 274 of the clutch mechanism 220 can be re-engaged in the elongated slots 272 of the rotational knob 270. Thus, a user can turn the drive unit 50 to rotate the waveguide 180 including the end-effector 180' (sometimes referred to as a blade) with respect to the clamp mechanism 220 to orient the narrow edge 191a or the broad edge 191b of the end-effector 180' with the pad of the clamp mechanism. This allows the surgeon to create different tissue effects by utilizing different configurations of the end-effector 180' without replacing the end-effector 180' or changing the clamp coagulator apparatus. For example, the broad edge 191b of the end-effector 180' coagulates more than it cuts, while the narrow surface 191a cuts faster but still causes coagulation of the tissue. It will be recognized that the end-effector 180' can have any suitable number of edges to cut or coagulate tissue (i.e., the end effector has three edges 120 degrees apart, four edges 90 degrees apart, etc.). The end-effector 180' may also receive suitable surface treatment, as is known in the art. After re-engagement of the clutch mechanism with the rotational knob 270, the clamp mechanism of the apparatus, the waveguide (including end-effector 180') and the associated ultrasonic drive unit 50 can be rotated, as a unit, with respect to housing 130. Such rotation is permitted prior to the operating lever 222 being moved, since lockout members 242 and 248 are respectively disengaged from notches 244 (of clutch mechanism 220) and notches 250 (of flange 252). Notches 244 and 250 are aligned and correspond in number with detent recesses 294 so that lockout members 242 and 248 can be respectively in the notches 244 and 250 in each of the indexed positions of the clamping mechanism and waveguides.

Figure 9:
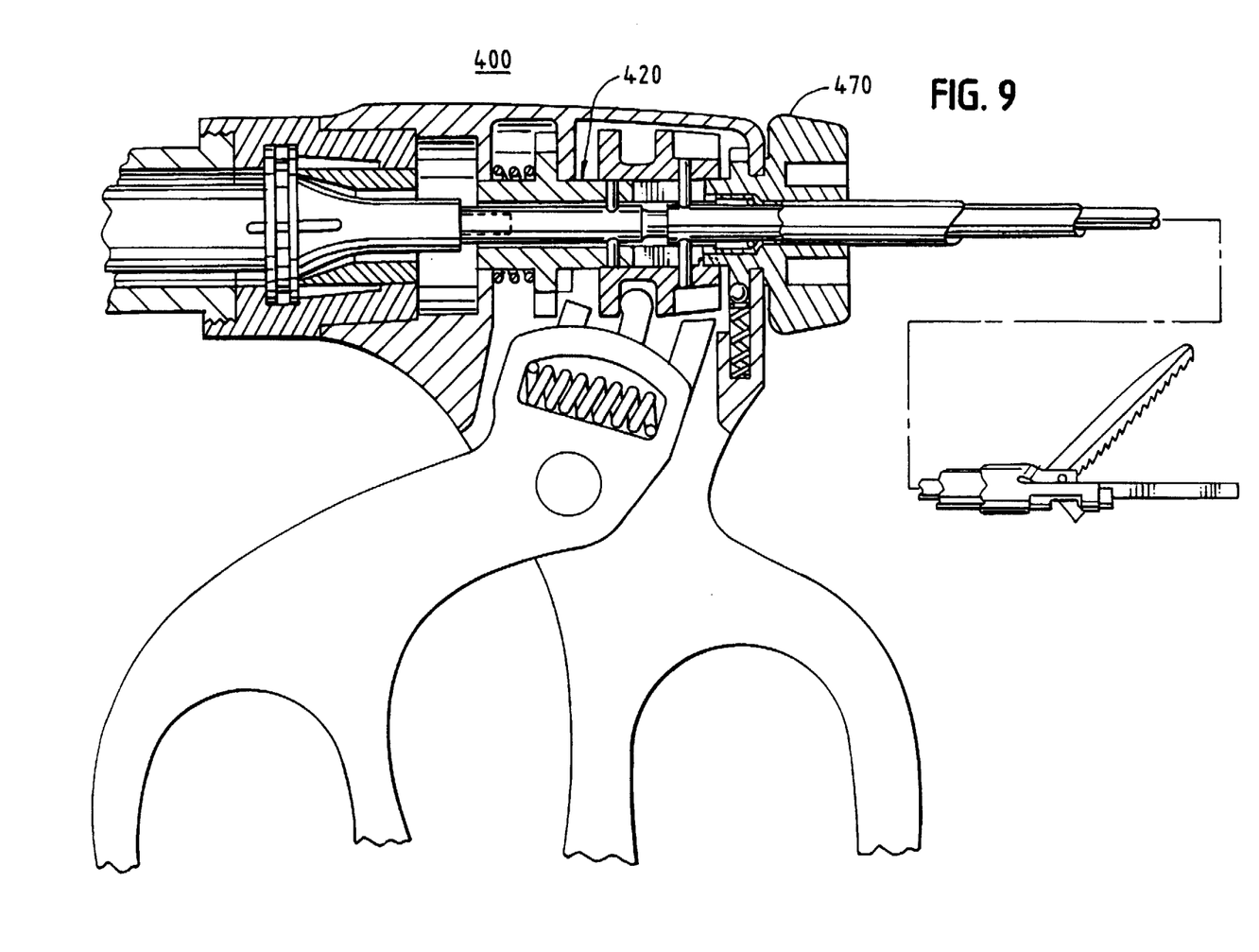
FIG. 9 is an enlarged, fragmentary view of another embodiment of a clamp coagulator apparatus.
Figure 10:
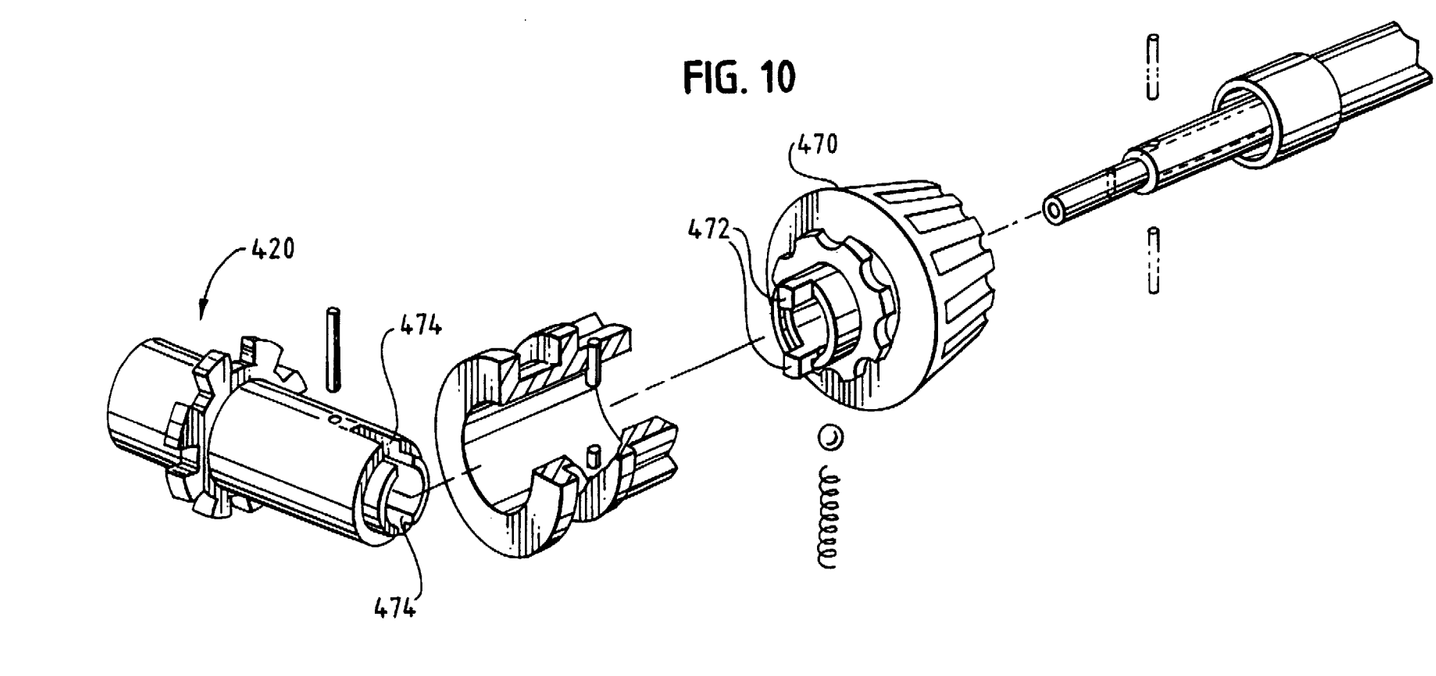
FIG. 10 is an enlarged, diagrammatic view illustrating an actuator collar, a rotational knob, and an clutch mechanism of the clamp coagulator apparatus of FIG. 9.

Referring now to FIGS. 9 and 10, another embodiment of a surgical system 400 is illustrated. The surgical system 400 corresponds, in many respects, in construction and function to the previously described surgical system of FIG. 1. Components of the surgical system 400 which generally corresponds to those components of the surgical system 100 of FIG. 1 are designated at in the four-hundred series. In this alternate embodiment, locking dogs 472 are provided on a rotational knob 470, while slots 474 for receiving the dogs 472 are provided on a reciprocable clutch mechanism 420. Thus, the driven surface of the clutch mechanism is provided by slots 494.

As shown in FIG. 10, the rotational knob 470 in FIG. 10 of the clamp coagulator apparatus has locking dogs 472 that interconnect with opposing slots 474 of the clutch mechanism 420. When the drive unit is rotated, the elongated portion is rotated causing the end-effector and clamp arm to turn together. When the drive unit is moved rearwardly, the clutch mechanism 420 slides rearwardly compressing the spring member 480 and disconnecting the opposing slots 474 from the dogs 472 of the knob 470. Thus, a selected edge of the end effector can be rotated into a desired operative position with respect to the clamp mechanism.

Referring now to FIGS. 1–4, the operation of the surgical system will be described below. When the physician is ready to use the clamp coagulator apparatus 120, the physician simply attaches the clamp coagulator apparatus 120 onto the drive unit 50. In order to join the clamp coagulator apparatus to the ultrasonic drive unit 50 in ultrasonic-transmitting relationship, the proximal portion of the outer tubular sheath 160 is preferably provided with a pair of wrench flats (not shown). The wrench flats allow torque to be applied by a suitable torque wrench or the like to thereby permit the waveguide 180 to be joined to the mounting device of the ultrasonic drive unit 50.

The surgeon can then rotate the rotational knob 270 to adjust the end-effector 180' and the clamp mechanism at a desired angular position. The ultrasonic drive unit, as well as the elongated portion 150, are thus rotatable, as a unit, by suitable manipulation of the rotation knob 270, relative to the housing 130 of the apparatus. As the knob 270 is rotated, the ball of the detent mechanism slips over the recesses of the flange of the knob 270 into adjacent recesses. As a result, the surgeon can position and maintain the clamp mechanism and end-effector at a desired orientation.

Once the clamp coagulator apparatus 120 is attached to the drive unit 50, the surgeon may rotate the end effector 180' with respect to the clamp mechanism to position a desired edge of the end effector in opposition to the clamp pad of the clamp arm. With the clamp arm in an open position, the surgeon can pull back on the drive unit 50 to compress the spring member 280 and disengage the dogs 274 of the clutch mechanism 220 from the slots 272 of the rotational knob 270. The surgeon can then rotate the drive unit 50 relative to the housing 130 of the clamp coagulator apparatus until the dogs 274 are biased back into the slots 272 by the spring member 280 thereby positioning a selected blade edge in operation with the clamp arm.

The surgeon can then move the surgical instrument to the surgical site. The end-effector 180' can then be inserted into an incision or port in the body of a patient to deliver ultrasonic energy to selected tissue. The clamp arm can be operated by moving the operating lever 222. When the operating lever 222 is moved toward the finger grip, the actuator collar 200 slides toward the handgrip portion to move the actuating member 170 rearwardly, thereby pivoting the clamping mechanism into its closed position. The movement of the operating lever 222 in the opposite direction moves the actuator collar 200 to cause the actuator member to slide in the opposite direction, i.e., forwardly, and hence pivot the clamping mechanism into its open position. The clamp mechanism can be rotated with respect to the housing and the end-effector can be rotated with respect to the clamp mechanism as desired by the surgeon.

Thus, the present surgical clamp coagulator apparatus is configured for highly efficient and versatile use, with the construction being sufficiently straight-forward and economical in configuration to permit single-patient use. Components of the apparatus can be fabricated from materials suited for surgical applications. By virtue of the detent mechanism provided by cooperation of the rotational knob, selective angular positioning of the elongated portion of the apparatus, and the associated ultrasonic drive unit, is readily effected with respect to the housing of the apparatus. The detent mechanism resists rotation of the ultrasonic drive unit, and associated cable assembly, with respect to the housing 130 with the resistance to rotation readily and conveniently overcome by application of sufficient torque via rotation knob 216.

The clutch mechanism allows rotation of the end-effector with respect to the clamp arm to align a desired edge of the end-effector with the clamp pad, with the clamping mechanism, ultrasonic waveguide, and ultrasonic drive unit thereafter be selectively rotatably positioned in an indexed fashion with respect to the apparatus housing. The scissors-like action provided by pivotal operating lever and cooperating handgrip portion facilitates convenient and efficient manipulation and positioning of the apparatus, and operation of the clamping mechanism at the distal portion of the apparatus whereby tissue is efficiently urged against the end-effector.

The surgical system can be used to coagulate and cut tissue when ultrasonic energy is applied, grasp tissue without application of ultrasonic energy, coagulate/cut with the clamp assembly open and tissue unclamped, probe or manipulate tissue without application of ultrasonic energy, and to dissection tissue with the clamp mechanism closed.

From the foregoing, it will be observed that numerous modifications and variations can be effected without departing from the true spirit and scope of the novel concept of the present invention. It is to be understood that no limitation with respect to the specific embodiment illustrated herein is intended or should be inferred. The disclosure is intended to cover, by the appended claims, all such modifications as fall within the scope of the claims.

What is claimed is:

1. An ultrasonic surgical instrument comprising:

a clamp coagulator apparatus having a housing;

a drive unit attachable to the housing;

an outer tubular sheath having a proximal end rotatably joined to said housing, and a distal end;

an actuating member reciprocally positioned within said outer tubular sheath to rotate therewith with respect to said housing;

an ultrasonic waveguide positioned within said outer tubular sheath and having an end-effector extending distally of said distal end of said outer tubular sheath;

a clamp arm pivotally mounted on said distal end of said outer tubular sheath to pivotally move with respect to said end-effector to clamp tissue between said clamp arm and said end-effector, said clamp arm being operatively connected to said actuating member so that reciprocable movement of said actuating member pivotally moves said clamp arm with respect to said end-effector;

an operating lever pivotally mounted on said housing;

an actuator collar interconnecting said operating lever with said actuating member so that pivotal movement of said operating lever reciprocally moves said actuating member for pivotally moving said clamp arm;

a rotational knob mounted on the outer tubular sheath to effect rotation of the outer sheath; and a clutch mechanism coupled to the waveguide for rotational movement therewith, the clutch mechanism having a distal end to cooperatively engage with the rotational knob such that rotational movement of the knob causes rotation movement of the clutch mechanism, the waveguide, and the clamp arm, the clutch mechanism also being movable to be disengaged from the rotational knob when the drive unit is moved proximally such that rotation of the drive unit rotates the clutch mechanism to turn the waveguide relative to the clamp arm.

2. The ultrasonic surgical apparatus in accordance with claim 1, including at least one detent member to index the rotational movement of the rotational knob and tubular outer sheath with respect to said housing.

3. The ultrasonic surgical apparatus in accordance with claim 1, wherein one of said clutch mechanism and said rotational knob includes a dog, and the other includes an opening for receiving said dog.

4. The ultrasonic surgical apparatus in accordance with claim 1, wherein the actuator collar includes a pair of circumferential flanges defining a circumferential slot.

5. The ultrasonic surgical apparatus in accordance with claim 4, wherein the operating lever includes a drive lug cooperating with the circumferential slot to reciprocally move the actuator collar.

6. The ultrasonic surgical apparatus in accordance with claim 1, wherein the operating lever includes at least one lockout member, the lockout member cooperating with one of the clutch mechanism and the actuator collar to prevent movement of the waveguide when the clamp arm is in a closed position.

7. An ultrasonic surgical clamp coagulator apparatus comprising:

a housing;

an outer sheath having a proximal end rotatably joined to said housing, and a distal end;

a rotational knob mounted on said outer sheath to effect rotation of the outer sheath with respect to said housing;

an actuating member reciprocally positioned within said outer tubular sheath to rotate therewith with respect to said housing;

an ultrasonic waveguide positioned within said outer tubular sheath and having an end-effector extending distally of said distal end of said outer tubular sheath;

a clamp arm pivotally mounted on said distal end of said outer tubular sheath to pivotally move with respect to said end-effector to clamp tissue between said clamp arm and said end-effector, said clamp arm being operatively connected to said actuating member so that reciprocable movement of said actuating member pivotally moves said clamp arm with respect to said end-effector;

an operating lever pivotally mounted on said housing;

an actuator collar interconnecting said operating lever with said actuating member so that pivotal movement of said operating lever reciprocally moves said actuating member for pivotally moving said clamp arm; and a clutch mechanism having a driven surface biased against the rotational knob so that rotation of the knob moves the clamp arm and waveguide relative to the housing, the clutch mechanism reciprocally movable to disengage the driven surface from the rotational knob so that rotation of the clutch mechanism rotates the end effector with respect to the clamp arm.

8. The ultrasonic surgical clamp apparatus in accordance with claim 7, further comprising a detent mechanism to index the rotational movement of the rotational knob with respect to said housing.

9. The ultrasonic surgical clamp apparatus in accordance with claim 7, wherein said driven surface of the clutch mechanism further comprises at least one dog cooperatively engageable with said rotational knob.

10. The ultrasonic surgical clamp apparatus in accordance with claim 7, further comprising at least one connector pin to couple the actuator collar to the actuating member.

11. An ultrasonic surgical clamp apparatus comprising:

a housing;

an outer sheath rotatably coupled to the housing;

an ultrasonic waveguide positioned within the outer sheath, the waveguide having an end-effector; and a clutch mechanism coupled to the waveguide, the clutch mechanism having a first rotational position such that rotation of the clutch mechanism causes rotation of the outer sheath and the end-effector relative to the housing and a second rotational position such that the rotation of the clutch mechanism causes rotation of the end effector relative to the outer sheath.

12. The ultrasonic surgical clamp apparatus in accordance with claim 11, further comprising a surgical tool mounted on the outer sheath, the surgical tool being operable by an operating lever coupled to the housing.

13. The ultrasonic surgical clamp apparatus in accordance with claim 12, wherein the surgical tool comprises a clamp arm.

14. The ultrasonic surgical clamp apparatus in accordance with claim 12, further including a rotational knob mounted on said outer sheath.

15. The ultrasonic surgical clamp apparatus in accordance with claim 14, wherein the rotational knob has at least one slot configured to cooperate with at least one locking flange of the clutch mechanism.

16. The ultrasonic surgical clamp apparatus in accordance with claim 14, further comprising a spring member to bias the clutch mechanism against the end of the rotational knob.

17. The ultrasonic surgical clamp apparatus in accordance with claim 14, wherein the clutch mechanism is disengaged from the rotational knob by a force applied to the clutch member in a direction of propagation of ultrasonic vibration.

18. The ultrasonic surgical clamp apparatus in accordance with claim 11, further comprising a connector pin to couple the clutch mechanism to the waveguide.

19. The ultrasonic surgical clamp apparatus in accordance with claim 11, further comprising a detent mechanism to index the rotational movement of the outer sheath with respect to said housing.

20. The ultrasonic surgical clamp apparatus in accordance with claim 19, wherein the detent mechanism comprises a ball biased by a spring against a detent receiving surface of the apparatus.

21. The ultrasonic surgical clamp apparatus in accordance with claim 20, wherein said detent receiving surface defines a plurality of detent receiving depressions, said apparatus including a lockout member positionable in one of a plurality of notches on said clutch mechanism, said notches being aligned with and corresponding in number to said depressions.

22. The ultrasonic surgical clamp apparatus in accordance with claim 11, further comprising an inner actuating member reciprocally positioned within said outer sheath.

23. The ultrasonic surgical clamp apparatus in accordance with claim 11, further comprising a ultrasonic drive unit coupled to the housing for driving said waveguide.

24. The ultrasonic surgical clamp apparatus in accordance with claim 11, wherein said end-effector has at least two elongated edges spaced circumferentially from one another about an axis of the end-effector extending generally parallel a longitudinal axis of the ultrasonic waveguide.

25. A method of applying ultrasonic energy to tissue of a patient comprising the steps of:

providing a clamp coagulator apparatus having a housing and an outer sheath extending therefrom, the outer sheath having an end effector extending therefrom and a surgical tool to cooperatively engage with the end-effector;

rotating the end effector with respect to the surgical tool; and rotating the end effector and surgical tool with respect to the housing of the clamp coagulator;

vibrating the end effector at a selected ultrasonic frequency; and contacting the tissue of the patient with the end effector.

26. The method of claim 25 further comprising the steps of selectively displacing said surgical tool toward and away from said end-effector.

* * * * *